United States Patent [19]

Eriksson et al.

[11] 4,118,485

[45] Oct. 3, 1978

[54] NON-THROMBOGENIC MEDICAL ARTICLE AND A METHOD FOR ITS PREPARATION

[75] Inventors: Jan-Christer Eriksson, Djursholm; Rolf Larsson, Ekero; Åke Rosengren, Enskede; Maj-Britt Hjelte, Huddinge, all of Sweden

[73] Assignee: Aminkemi Aktiebolag, Broma, Sweden

[21] Appl. No.: 666,943

[22] Filed: Mar. 15, 1976

[30] Foreign Application Priority Data

Mar. 20, 1975 [SE] Sweden .......................... 75/032409

[51] Int. Cl.² ..................... A61K 31/725; C07G 11/00
[52] U.S. Cl. ......................................... 424/183; 536/1
[58] Field of Search .................. 424/183; 427/2, 3, 4; 117/47 A; 536/1, 4

[56] References Cited

U.S. PATENT DOCUMENTS

| 3,617,344 | 11/1971 | Leininger et al. | 424/183 |
| 3,634,123 | 1/1972 | Eriksson et al. | 117/47 A |
| 3,810,781 | 5/1974 | Eriksson et al. | 117/47 A |

FOREIGN PATENT DOCUMENTS 2,148,011  4/1972  Fed. Rep. of Germany .............. 427/2

*Primary Examiner*—Henry R. Jiles
*Assistant Examiner*—Cary Owens
*Attorney, Agent, or Firm*—Brumbaugh, Graves, Donohue & Raymond

[57] ABSTRACT

A medical article is made non-thrombogenic by means of a surface coating containing heparin. The heparinized surface is stabilized by being contacted first with a cationic surfactant of the primary amine type and, subsequently, with a dialdehyde.

25 Claims, No Drawings

NON-THROMBOGENIC MEDICAL ARTICLE AND A METHOD FOR ITS PREPARATION

In the field of medicine considerable attention has been paid during the last decade to problems connected with the use of artificial materials coming into contact with blood. Upon contact with a foreign surface blood reacts in a similar way as in the case of damage to a blood vessel: subsequent to protein adsorption and thrombocyte adhesion, thrombocyte aggregation and coagulation occur. Consequently, a foreign surface may cause thrombus formation which constitutes a risk of clinical complication.

With the object of reducing the risk of complications connected with the contact of artificial materials with blood, efforts have been made to produce so-called thrombo-resistant or non-thrombogenic surfaces which are compatible with blood. One line of research has been based on the idea of binding heparin to the surface, heparin being a well-known and much utilized anti-coagulant which in most cases exists in the form of its sodium salt. Stable covalent binding of heparin to different substrates has been attempted. However, it has not yet been possible to perform a covalent binding reaction without simultaneous loss of the physiological activity of the heparin. An alternative method that is based on ion-linking the negative heparinate ions to a surface containing positive cationic groups has the advantage that it does not cause any loss of the physiological activity of the heparin, but on the other hand it has been established that heparin which has only been ion-linked to a surface containing cationic groups is released to some extent upon contact with plasma or blood, i.e. the ionogenic bond is not sufficiently stable (see G. A. Grode, R. D. Falb and J. P. Crowley, J. Biomed. Mater. Res. Symposium, No. 3 (1972), page 77 and R. Cramer, R. Moore and K. Amplatz, Radiology 109, 585 (1973).

Swedish Pat. No. 365,710 and the corresponding U.S. Pat. No. 3,810,781 describe a method for stabilizing heparin which is ion-linked to cationic groups in a plastic surface. This method is based on the idea of producing cross-links between the heparin molecules, thus preventing release of the heparin from the surface. A dialdehyde, primarily glutardialdehyde, has been used as the cross-linking agent.

Subsequent testing of this stabilizing treatment with dialdehyde has shown that differences exist in the stabilizing effect when different cationic groups are used for ion-linking heparin to the plastic surface. The use of cationic groups of the primary amine type, i.e. primary ammonium groups, has been found to result in improved stability of the heparinized surface treated with dialdehyde as compared with the use of secondary, tertiary or quaternary ammonium groups.

On the basis of these results continued research has now revealed that an improved stabilization of the heparinized surface is obtained if the anionic groups of the heparin are blocked with a cationic surfactant of the primary amine type and then treated with a dialdehyde to form Schiff's bases in the heparinized surface, said Schiff's bases having a low solubility in water, and to partially unblock the anionic groups of the heparin.

A Schiff's base is a chemical compound containing the characteristic group

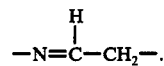

It is well-known that a Schiff's base is formed upon the reaction between an aldehyde and a primary amine, but not between an aldehyde and a secondary, tertiary or quaternary amine. Without wanting to commit ourselves to any particular theory on the reactions producing the improved stabilization of the invention, we shall illustrate below how we imagine that the stabilization is achieved.

When a primary amine $RNH_2$, in which R is alkyl, reacts with a dialdehyde, such as glutardialdehyde OHC—$CH_2$—$CH_2$—$CH_2$—CHO, the following two compounds may be formed:

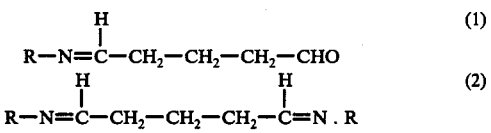

Both compounds are Schiff's bases. The compound (1), however, has some solubility in water, whereas the compound (2) has a very low water solubility. We believe that compounds of type (2), containing no unreacted aldehyde groups, are responsible for the stabilization.

The heparin molecule contains various anionic groups, such as —$OSO_3^-$ and —$NSO_3^-$, which can react with e.g. primary alkyl ammonium ions to form ionogenic bonds. The reaction can be illustrated in this way, the heparinate ion being merely referred to as $HEP^{n-}$ for the sake of simplicity:

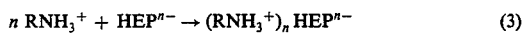

The anionic groups of the heparin molecule have thus been "blocked" by the primary alkyl ammonium ions. The reaction of said blocked heparin with the dialdehyde can be illustrated in this way; the dialdehyde being glutardialdehyde:

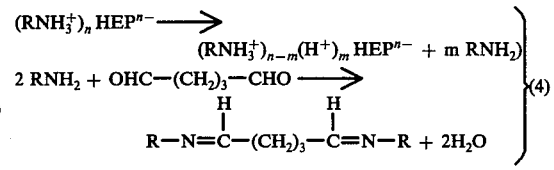

The first step of the reaction (4) results in a partial "unblocking" of the heparin, thus restoring its physiological activity, and formation of primary alkyl amine. The second step of the reaction (4) results in the formation of the Schiff's base of the type shown in the formula (2) above. The molecules of said Schiff's base (2) will be interspersed among the heparin molecules. They have a hydrophobic nature, and this is, to the best of our understanding, the reason why they prevent the heparin from being dissolved. In other words: the molecules of the Schiff's base constitute a steric hindrance for the removal of the heparin molecules.

It is likely that a cross-linking reaction between the dialdehyde and the amino groups of two adjacent heparin molecules is also of some importance in achieving the stabilization of the heparin. Said cross-linking reaction can be illustrated as follows.

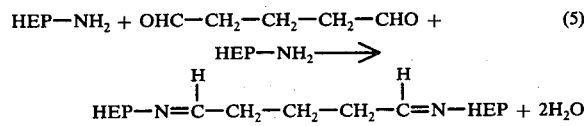

According to a first embodiment of the invention a heparinized surface is first treated with an aqueous solution of a primary amine in the form of a corresponding ammonium salt, and is subsequently stabilized by being treated with an aqueous solution of a dialdehyde. According to a second embodiment of the invention heparin in an aqueous solution is reacted with a primary amine in the form of a corresponding ammonium salt, to form a heparin-alkylammonium complex compound having a low solubility. Said complex compound is dissolved in an organic solvent, the solution is applied onto the surface to be heparinized, and the solvent is allowed to evaporate, leaving a heparin-alkylammonium complex coating on the surface. Said coating is now stabilized by being treated with an aqueous solution of a dialdehyde.

We shall now briefly describe five useful methods for producing a heparinized surface in which the heparin has an inadequate stability which can be improved by means of the present invention. A more complete survey of heparinization methods has been presented by R. G. Guidon, P. Bergeron and J. A. Awad in L'Union Medical du Canada, 103, 71 (1974).

(1) A plastic surface is first treated with a cationic surfactant solution, and thereafter with a heparin solution, in accordance with Swedish Pat. No. 306,597 or the corresponding U.S. Pat. No. 3,634,123 or according to G. A. Grode, S. A. Andersson, H. M. Grotta, R. D. Falb, Trans. Amer. Soc. Artif. Intern. Organs 15, 1 (1969).

(2) A complex compound of heparin and a cation surfactant of the quaternary amine type is dissolved in an organic solvent. The solution is applied on the surface of, for example, plastic, glass or metal, and the solvent is evaporated. Vide G. A. Grode, R. D. Falb, J. P. Crowley, J. Biomed. Mater. Res. Symposium, 3, 77 (1972) and Amplatz, K., Invest. Radiol. 6, 280 (1971). A solution of this type, consisting of the complex compound of heparin and benzalkonium chloride dissolved in isopropyl alcohol, is commercially available.

(3) A plastic material is produced containing polymer chains to which quaternary cationic groups are chemically linked. Alternatively, quaternary cationic groups are linked covalently to the plastic surface by means of a chemical reaction, for example in accordance with U.S. Pat. No. 3,617,344. After that heparin is ion-linked to the cationic groups in the plastic surface by treating with heparin solution.

(4) A coupling agent of the amino-silane type is first linked to the surface to be heparinized. Subsequently, the surface is treated with a heparin solution.

(5) A concentrated water solution of heparin is applied to the surface to be heparinized, and the water is then evaporated so that a coherent heparin film is formed on the surface. Such heparin coating has been used for glass tubes intended for certain clinical analysis of blood when coagulation of the blood must be prevented.

In the heparinization methods (2), (3) and (5) primary amino or ammonium groups are not added. The components of the heparinized surface are in method (2) heparin and a cationic surfactant of the quaternary amine type, in method (3) heparin and quaternary ammonium groups, and in method (5) only heparin. In the heparinization method according to method (1) primary alkyl ammonium groups are added only in certain cases, viz. when a solution of a cationic surfactant of the primary amine type is used for the first stage of the treatment. In heparinization method (4) primary amino groups are usually added. In heparinized surfaces produced by the methods (1) and (4), while adding primary amine, the number of primary amino or ammonium groups in the surface will be comparatively low. This is so because said surfaces have been treated first with the primary amine agent, and subsequently with the heparin. Because of the low number of primary amino or ammonium groups said surfaces cannot be satsifactorily stabilized solely by being treated with a dialdehyde.

A heparinized surface produced by any of the methods (1)–(5) above can be stabilized by means of the present invention. It is desired that the heparinized surface is first treated with the primary amine agent at such conditions that substantially all the anionic groups of the heparin are blocked by the alkyl ammonium ions, and that the surface is subsequently treated with the dialdehyde. This stabilization treatment results in a heparinized surface in which the heparin has its full physiological activity and is not released from the surface upon contact with blood or blood plasma. It is possible to produce stabilized heparin coatings not only upon plastic articles. Methods (2), (4) and (5) make it possible to produce such coatings also upon glass and metal articles.

In the heparinization method (2) above the surface layer consists of a complex compound of heparin and a quaternary ammonium surfactant. When said complex compound is contacted with an aqueous solution of a cationic surfactant of the primary amine type, an exchange reaction takes place which results in the formation of a complex between the heparin and said surfactant, while the quaternary ammonium surfactant is removed from the surface. This is so because the solubility of the primary alkylammonium-heparin complex is lower than that of the quaternary alkylammonium-heparin complex. The exchange reaction described means, therefore, that the anionic groups of heparin are blocked by long-chained alkyl ammonium cations.

Cationic groups of the primary amine type can be added to the heparin even before the heparin is attached to the surface of the article. This is done by reacting the heparin, in an aqueous solution, with a primary alkylammonium salt to form a heparinalkylammonium complex compound having a low solubility. It is desired to let this reaction proceed so far that substantially all the anionic groups in the heparin molecule have reacted with the alkylammonium ions. The best way of having the reaction proceed so far as to produce complete blocking is to have the alkylammonium salt present in a quantity at least corresponding to the number of heparin anionic groups which are present in the solution from which the comples is precipitated.

The complex compound thus formed is dissolved in a solvent, and the solution is applied on the article to be heparinized. The solvent is now evaporated, leaving a thin layer of the heparin-alkylammonium complex on the surface of the article. As a guarantee that all the anionic groups of the heparin have reacted with alkylammonium ions, the article can now be contacted with an aqueous solution of the alkyl ammonium salt. The heparinized surface is now stabilized by being contacted with an aqueous solution of the dialdehyde.

The solvent for the heparin-alkylammonium complex compound should be a mixture of a non-polar solvent, such as cyclohexane, and a polar solvent, such as a lower alcohol, e.g. ethanol or propanol. The heparin-alkylammonium complex compound is preferably dispersed in the non-polar solvent, and the polar solvent is added slowly. The complex compound first forms an emulsion in the non-polar solvent. A continued addition of the polar solvent results in the complex compound being dissolved. It is now preferred to add a small quantity of a solubilizer having a polarity between those of the two solvents, in order to make the solution stable and prevent phase separation. When using a mixture of cyclohexane and ethanol the solubilizer may be dichloroethane.

The importance of making a sufficiently large number of the anionic groups of the heparin react with the primary alkylammonium ions has been explained above. The degree of reaction can be examined by means of an indicator producing a characteristic color when reacting with heparin. We prefer to use toluidine blue which is a salt which readily dissolves in water, producing a blue solution. If a heparinized surface is contacted with said solution, the reaction between the toluidine blue and the anionic groups of the heparin produces a pink color. The intensity of said pink color is indicative of the physiological activity of the heparin. A more quantitative way of measuring the physiological activity is to measure spectrophotometrically the decrease in color intensity of the toluidine blue solution resulting from toluidine blue having been adsorbed by the heparinized surface. We prefer to let the reaction between the heparin and the primary alkylammonium ions proceed so far that no pink color can be observed when the surface is examined with the toluidine blue test.

The toluidine blue test is also useful for examining the heparinized surface after the stabilizing treatment with the dialdehyde, in order to make sure that a sufficient number of the anionic groups of the heparin have been unblocked. If a faint pink color can be observed, the unblocking process has been satisfactory. The toluidine blue test is also useful for examining whether the stabilization process has resulted in a satisfactory bonding of the heparin to the surface. The finished surface is contacted with blood or blood plasma for a period of 60 minutes. After rinsing the toluidine test is now repeated. If a reduced color intensity is observed, too much heparin has been released from the surface.

The toluidine blue test is very useful not only for examining the quality of the stabilized surface, but also for finding out the best reaction conditions for the treatment of the heparinized surface with the primary alkylammonium salt and for the stabilization treatment with the dialdehyde. By experimenting with various concentrations of the solutions, and with various temperatures and times of treatments, and checking the results with the toluidine blue test, the best conditions can be found.

Of the cationic surfactants of the primary amine type now commercially available, we have investigated the use according to the invention of, amongst others, alkyl amine hydrochlorides having 8–22 carbon atoms in the alkyl chain. We have found that cationic surfactants of the primary amine type having a critical micelle concentration ("CMC") of less than about $5 \cdot 10^{-3}$ mol/liter are capable of blocking the anionic groups in heparin so that the color reaction with toluidine blue does not occur. The use of such surfactants having a CMC less than about $5 \cdot 10^{-3}$ mol/liter, followed by a stabilization treatment with a dialdehyde leads to the formation of a sufficient quantity of Schiff's bases with a low solubility in the heparinized surface, therefore, and also to a partial unblocking of the anionic groups of the heparin.

The critical micelle concentration is the lowest concentration at which micellar aggregates occur in an aqueous solution of a surfactant. More information on the CMC can be found in, for example, Mukerjee & Mysels: Critical Micelle Concentrations of Aqueous Surfactant Systems, issued by the U.S. National Bureau of Standards (NSRDS-NBS 36).

We have found hexadecylamine hydrochloride (alternative name: cetylamine hydrochloride) to be a particularly useful cationic surfactant of the primary amine type. With the aid of the toluidine blue reaction described above we have studied the treatment conditions when using this surfactant for the stabilization of heparinized surfaces containing releasable heparin.

It has thus been determined that treatment of a heparinized surface with a water solution of cetylamine hydrochloride resulting in the desired stabilization effect can be performed within wide limits of temperature, time and concentration of the solution. However, it is preferable to perform the treatment under such temperature and concentration conditions that a clear solution of the cationic surfactant in question is obtained. If, therefore, a concentration below the critical micelle concentration (CMC for cetylamine hydrochloride is $\approx 10^{-3}$ mol/liter) is chosen, the treatment may be performed at room temperature. A concentration below $10^{-5}$ mol/liter is not generally suitable, since a relatively large volume of solution may have to be used in order to supply the surface with a sufficient quantity of the cationic surfactant. On the other hand, if it is expedient to use a smaller volume of solution and, therefore, a concentration between CMC and the saturation concentration has been chosen, a treating temperature higher than the Krafft temperature should be used. The surfactant is dissolved in water at a temperature above the Krafft temperature, thus forming a clear solution. For cetylamine hydrochloride the Krafft temperature is about 50° C. The specific conditions appropriate when using other cationic surfactants of the primary amine type can, mutatis mutandis, be determined in corresponding manner.

The reaction between the surface-linked heparin and the cationic surfactant of the primary amine type takes place so quickly in an aqueous solution that a treating time of a few minutes is generally quite sufficient. If the heparinized surface contains a complex compound of heparin and a surfactant of the secondary, tertiary or quaternary amine type the treatment with the solution of the surfactant of the primary amine type must normally be performed at a concentration above CMC and at a temperature above the Krafft temperature for a treatment time shorter than 15 minutes to be satisfactory.

The treatment with the dialdehyde may be performed in the manner described more fully in Swedish Pat. No. 365,710 and the corresponding U.S. Pat. No. 3,810,781, i.e. within the following limits with respect to time, temperature, concentration and pH-value in the solution:

Time: 1 minute–3 hours
Temperature: 20°–80° C.
Concentration: 0.1–25 percent by weight
pH-value: between 2 and 10

It is preferred to use a dialdehyde having the formula CHO—CHO or CHO—R—CHO where R represents 1–4 $CH_2$ groups. Glutardialdehyde is particularly preferred.

As in Swedish Pat. No. 365,710 and the corresponding U.S. Pat. No. 3,810,781, the dialdehyde may also be added in the form of the corresponding acetal.

The following examples give a more detailed description of the stabilization treatment of heparinized surfaces in accordance with the invention, and of the testing of the resulting surfaces for stability.

EXAMPLE 1

Stabilization of a heparinized surface produced by the use of a complex compound of heparin and a cationic surfactant of the quaternary amine type Polyethylene catheters were treated with a solution of heparin benzalkonium chloride complex dissolved in isopropanol (1000 IU heparin/ml). Benzalkonium chloride is a compound having the general formula

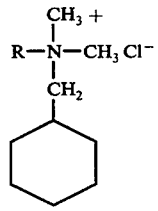

in which R is alkyl containing 8–18 carbon atoms. In the particular compound used in this Example, R contained 16 carbon atoms. After drying in air the catheters were treated with 10 mM of water solution of alkylamine hydrochloride having varying hydrocarbon chain length at 65° C. for 15 minutes. The samples treated in this way were then treated with a 0.5% water solution of glutardialdehyde at 55° C. for 20 minutes. Tests Nos. 1 and 2 refer to reference samples. Testing is based on measuring the color reaction with toluidine blue, and measuring the quantity of heparin released after 60 minutes in contact with blood plasma at room temperature, in accordance with Eika, Godal and Keirulf.

As can be seen from Table I, completely satisfactory results have been obtained with the use of alkylamine hydrochlorides having a chain length $C_{14}$ and greater. CMC for tetradecylamine hydrochloride ($C_{14}$) is about $5 \cdot 10^{-3}$ mol/liter, while CMC for dodecylamine hydrochloride ($C_{12}$) is about $10^{-2}$ mol/liter. Complete blocking of the anionic groups of the heparin is not obtained with hydrocarbon chain lengths of $C_{12}$ and shorter. In test No. 4 NaCl has been added during the treatment with glutardialdehyde. Such addition of NaCl has a favorable effect in this case, as can be seen, and reduces the heparin loss. Corresponding test results have been noted when heparinizing and stabilizing surfaces of other materials such as glass, metal and polytetrafluoroethylene.

TABLE I

| Test No. | Treatment with solution of alkylamine hydrochloride, 10 mM, 65° C, 15 min. | | Treatment with glutardialdehyde solution, 0.5% 55° C, 20 min. | Quantity of toluidine blue absorbed before glutardialdehyde treatment, expressed in equiv. quantity heparin mg/cm² | Quantity of toluidine blue absorbed after glutardialdehyde treatment, expressed in equiv. quantity heparin mg/cm² | Heparin loss in mg/cm² after 60 min. contact with blood plasma at room temperature |
|---|---|---|---|---|---|---|
| | Alkyl carbon chain | CMC mol/liter | | | | |
| 1 | — | — | — | $2.5 \cdot 10^{-2}$ | — | $0.5 \cdot 10^{-2}$ |
| 2 | — | — | + | $2.5 \cdot 10^{-2}$ | $8.1 \cdot 10^{-2}$ | $0.7 \cdot 10^{-2}$ |
| 3 | $C_{14}$ | $5 \cdot 10^{-3}$ | + | 0 | $4.4 \cdot 10^{-2}$ | $0.07 \cdot 10^{-2}$ |
| 4 | $C_{14}$ | $5 \cdot 10^{-3}$ | + (1MNaCl) | 0 | $4.6 \cdot 10^{-2}$ | $0.02 \cdot 10^{-2}$ |
| 5 | $C_{16}$ | $10^{-3}$ | + | 0 | $3.1 \cdot 10^{-2}$ | $0.02 \cdot 10^{-2}$ |

EXAMPLE 2

Treatment of a heparinized surface produced using a solution of a complex compound of heparin and alkylamine hydrochloride 300 mg heparin, corresponding to 40,000 IU was dissolved in 100 ml distilled water. This heparin solution was mixed with 100 ml hot (60° C.) 17.6 mM water solution of alkylamine hydrochloride. A complex compound of heparin and alkylamine hydrochloride, having a low solubility, was formed. Said complex compound was separated from the solution by means of centrifugal force and was then dispersed into 120 ml cyclohexane. 64 ml ethanol was then slowly added, stirring all the time. Finally 40 ml dichloroethane was added, after which the solution was filtered. The resultant heparin content in the solution was 165 IU/ml = 1.25 mg/ml. In this way several solutions were prepared containing complex compounds of heparin and alkylamine hydrochlorides of various hydrocarbon chain lengths.

Polyethylene catheters were treated by being dipped in the solutions thus produced. The solvent was removed by evaporation. Stabilization treatment was then performed using 0.5% glutardialdehyde solution in water at 55° C. for 20 minutes. The surfaces were tested by measuring the adsorption of toluidine blue on the surfaces before and after the stabilizing treatment and after 15 minutes exposure to 25% NaCl solution at room temperature: The last mentioned test is useful because a 25% NaCl solution dissolves heparin from a heparinized surface which has been insufficiently stabilized.

As can be seen from Table 2, completely satisfactory results have been obtained using complex compounds of heparin and alkyl amine hydrochlorides having an alkyl chain length of $C_{14}$ or more. It is also clear from the Table, that blocking of the anionic groups of the heparin was produced by the alkylamine hydrochlorides having CMC $\approx 5 \cdot 10^{-3}$ mol/liter and below. The stabilization effect is satisfactory for $C_{14}$-amine hydrochloride with CMC = $5 \cdot 10^{-3}$ when NaCl is added during the glutardialdehyde treatment. Corresponding test results have been obtained when heparinizing and stabilizing surfaces of other materials, such as glass, metal and polytetrafluoroethylene.

TABLE 2

| | Complex compound of heparin and alkylamine hydrochloride having | | Treatment with glutardialdehyde solution 0.5%, 55° C, 20 min. | Quantity of toluidine blue absorbed, expressed in equivalent quantity heparin mg/cm² | | |
|---|---|---|---|---|---|---|
| Test No. | carbon chain length | CMC mol/liter | | before treatment with glutardialdehyde | after treatment with glutardialdehyde | after treatment with 25% NaCl solution |
| 1 | $C_{12}$ | $10^{-2}$ | + | $6.6 \cdot 10^{-2}$ | $3.1 \cdot 10^{-2}$ | 0 |
| 2 | $C_{14}$ | $5 \cdot 10^{-3}$ | + | 0 | $2.8 \cdot 10^{-2}$ | 0 |
| 3 | $C_{14}$ | $5 \cdot 10^{-3}$ | +(1 MNaCl) | 0 | $2.4 \cdot 10^{-2}$ | $2.3 \cdot 10^{-2}$ |
| 4 | $C_{16}$ | $10^{-3}$ | + | 0 | $2.0 \cdot 10^{-2}$ | $1.3 \cdot 10^{-2}$ |
| 5 | $C_{18}$ | $4 \cdot 10^{-4}$ | + | 0 | $1.6 \cdot 10^{-2}$ | $2.5 \cdot 10^{-2}$ |
| 6 | $C_{22}$ | $4 \cdot 10^{-5}$ | + | 0 | $1.1 \cdot 10^{-2}$ | $0.5 \cdot 10^{-2}$ |

EXAMPLE 3

Stabilizing a heparinized surface produced by treating the surface first with a solution of cetylamine hydrochloride and then with a heparin solution The heparinization was performed in accordance with Swedish Pat. No. 306,597 and the corresponding U.S. Pat. No. 3,634,123. Polyethylene and polyurethane catheters were treated first at 75° C. for 15 minutes with a 0.5 mM cetylamine hydrochloride solution in water and thereafter at 70° C. for 45 minutes with a 10 IU/ml water solution of heparin. The catheters were now again treated with an aqueous solution of alkylamine hydrochloride viz. with 0.5 mM solutions of cetylamine hydrochloride or octadecylamine hydrochloride at 60° C. for 15 minutes. The stabilization treatment was now performed with 0.5% glutardialdehyde solution for 20 minutes at 55° C. The catheters treated in this manner were compared with catheters subjected to the same treatment with the exception of the treatment with cetylamine hydrochloride or octadecylamine hydrochloride. As can be seen from Table 3, treatment with $C_{16}$ and $C_{18}$ amine hydrochloride solution prior to the stabilization treatment resulted in a considerable reduction in the heparin loss upon contact with blood plasma or 25% NaCl solution.

vent substantial release of heparin from said surface coating upon contact with blood.

2. A medical article as claimed in claim 1, in which the dialdehyde is taken from the group consisting of OHC—CHO and OHC—R—CHO in which R represents 1-4 $CH_2$ groups.

3. A medical article as claimed in claim 2, in which the dialdehyde is glutardialdehyde, OHC—$(CH_2)_3$—CHO.

4. A medical article as claimed in claim 1, in which the primary amine is of the type $RNH_2$ in which R is alkyl with 14-22, preferably 16-18 carbon atoms.

5. A medical article as claimed in claim 1, in which the ammonium salt of the primary amine has a critical micelle concentration lower than $5 \cdot 10^{-3}$ mol/liter.

6. The method of stabilizing a heparinized surface to prevent release of heparin upon contact with blood, comprising treating the heparin with a cationic primary amine surfactant to block the anionic groups of the heparin and contacting the surface containing such blocked heparin with a dialdehyde to form in said surface Schiff's bases having a low solubility and to partially unblock the anionic groups of the heparin.

7. The method as claimed in claim 6, comprising reacting heparin with a cationic primary alkylammonium salt to form an insoluble complex compound in

TABLE 3

| Test No. | Catheter material (trade mark) | Treatment with alkylamine hydrochloride after heparization and bafore stabilization with glutardialdehyde: Alkyl carbon chain: | Heparin loss after contact with blood plasma for 15 min. at room temperature (IU per cm²) | Heparin loss after contact with 25% NaCl solution for 10 min. at 40° C (IU per cm²) |
|---|---|---|---|---|
| 1 | Polyethylene (Kifa) | — | 1.6 | — |
| 2 | Polyethylene (Kifa) | $C_{16}$ | 0.02 | — |
| 3 | Polyurethane (Cordis) | — | 0.2 | — |
| 4 | Polyurethane (Cordis) | $C_{16}$ | 0.02 | — |
| 5 | Polyethylene (Portex) | — | — | 0.14 |
| 6 | Polyethylene (Portex) | $C_{18}$ | — | 0.03 |
| 7 | Polyethylene (Surgimed) | — | 0.26 | — |
| 8 | Polyethylene (Surgimed) | $C_{16}$ | 0.01 | — |

We claim:

1. A medical article for use in contact with blood having a surface coating containing heparin to prevent thrombosis upon contact with blood, said surface coating also containing Schiff's bases with low solubility formed by the reaction of a dialdehyde and a primary amine, the molecules of said Schiff's bases being interspersed between the heparin molecules having partially blocked anionic groups in said surface coating to prevent substantial release of heparin from said surface coating upon contact with blood.

which the anionic groups of the heparin are blocked by said cationic salt, dissolving said complex compound in a mixed organic solvent containing a non-polar and a polar solvent, contacting the surface with the solution thus produced to form a liquid film coating on the surface, evaporating the solvent from said coating, and contacting said coating with an aqueous solution of the dialdehyde.

8. The method as claimed in claim 6, comprising treating the heparin with the cationic primary amine surfactant until a substantially complete blocking of all anionic groups of the heparin has taken place, as indicated by the absence of pink color when testing with toluidene blue in accordance with the toluidene blue test.

9. The method as claimed in claim 6 characterized in that a cationic primary amine surfactant is used having a critical micelle concentration which is lower than about $5 \cdot 10^{-3}$ mol/liter.

10. The method as claimed in claim 9, comprising treating the heparin with an aqueous solution of the cationic primary amine surfactant in a concentration exceeding the critical micelle concentration, at a temperature exceeding the Krafft temperature.

11. The method as claimed in claim 6, comprising treating the heparin with an alkyl amine hydrochloride having 14 to 22, preferably 16 to 18, carbon atoms in the alkyl group.

12. The method as claimed in claim 6, comprising treating the surface containing blocked heparin with glutardialdehyde.

13. The method as claimed in claim 6 for stabilizing a heparin layer linked by means of ionic bonds to a polymer surface comprising contacting the heparin layer with a 0.5 mM aqueous solution of cetyl amine hydrochloride or octadecyl amine hydrochloride at 60° C. for 15 minutes and contacting the surface thus produced with a 0.5% aqueous solution of glutardialdehyde at 55° C. for 20 minutes.

14. The method as claimed in claim 7, comprising mixing 100 parts by volume of an aqueous solution of heparin containing 300 mg (40,000 IU) per 100 ml at 60° C. with 100 parts by volume of 17.6 millimole per liter aqueous solution of an alkyl amine hydrochloride having 16–18 carbon atoms in the alkyl chain, separating the resulting insoluble complex compound of heparin and alkyl amine hydrochloride from the solution, dispersing said complex compound in 120 parts by volume of cyclohexane, gradually adding 64 parts by volume of ethanol while stirring, adding 40 parts by volume of dichloroethane to the solution thus produced, filtering the resulting solution, applying the solution thus obtained to the surface of an article to be made non-thrombogenic so as to form a surface coating on said article, evaporating the solvent from said surface coating, and contacting the surface coating with a 0.5% aqueous solution of glutardialdehyde at 55° C. for 20 minutes.

15. An article as claimed in claim 1 in which the heparinized surface is produced by using a solution of a complex compound of heparin and a cationic surfactant of the quaternary amine type.

16. An article as claimed in claim 1 in which the heparinized surface is produced by using a solution of a complex compound of heparin and alkyl-ammonium salt.

17. An article as claimed in claim 1 in which the heparinized surface is produced by treating the surface first with a solution of an alkyl-ammonium salt and then with a heparin solution.

18. The method as claimed in claim 6 wherein the heparinized surface is produced by using a solution of a complex compound of heparin and a cationic surfactant of the quaternary amine type.

19. The method as claimed in claim 6 wherein the heparinized surface is prepared using a solution of a complex compound of heparin and alkyl-ammonium salt.

20. The method of claim 6 wherein the heparinized surface is prepared by treating the surface first with a solution of an alkyl-ammonium salt and then with a heparin solution.

21. An article having a heparinized surface prepared by the method of claim 6.

22. An article having a heparinized surface prepared by the method of claim 8.

23. An article having a heparinized surface prepared by the method of claim 11.

24. An article having a heparinized surface prepared by the method of claim 9.

25. A medical article according to claim 1 wherein the amount of the Schiff's bases contained in the surface coating is such that the release of heparin from said surface coating after contact with blood for about 15 minutes at room temperature is not more than about 0.02 IU per square centimeter surface.

* * * * *

UNITED STATES PATENT OFFICE
CERTIFICATE OF CORRECTION

Patent No. 4,118,485  Dated October 3, 1978

Inventor(s) Jan-Christer Eriksson et al.

It is certified that error appears in the above-identified patent and that said Letters Patent are hereby corrected as shown below:

Column 3, line 8, before "HEP-N" insert -- ⟶ --;
Column 9, line 3 of TABLE 3, heading, "heparization and before" should read -- heparinization and before --.

Signed and Sealed this

Thirteenth Day of March 1979

[SEAL]

Attest:

RUTH C. MASON
Attesting Officer

DONALD W. BANNER
Commissioner of Patents and Trademarks